(12) United States Patent
Poulle

(10) Patent No.: US 8,729,244 B2
(45) Date of Patent: May 20, 2014

(54) METHOD FOR PURIFYING FACTOR B

(75) Inventor: Michel Poulle, Wavrin (FR)

(73) Assignee: Laboratoire Francais du Fractionnement et des Biotechnologies, Les Ulis (FR)

( * ) Notice: Subject to any disclaimer, the term of this patent is extended or adjusted under 35 U.S.C. 154(b) by 0 days.

(21) Appl. No.: 13/510,140

(22) PCT Filed: Nov. 15, 2010

(86) PCT No.: PCT/FR2010/052426
§ 371 (c)(1),
(2), (4) Date: May 16, 2012

(87) PCT Pub. No.: WO2011/058286
PCT Pub. Date: May 19, 2011

(65) Prior Publication Data
US 2012/0232253 A1 Sep. 13, 2012

(30) Foreign Application Priority Data

Nov. 16, 2009 (FR) ..................................... 09 58047

(51) Int. Cl.
| | | |
|---|---|---|
| *A61K 38/00* | (2006.01) | |
| *C07K 1/22* | (2006.01) | |
| *C07K 1/36* | (2006.01) | |
| *C07K 1/18* | (2006.01) | |
| *A61K 38/42* | (2006.01) | |
| *C07K 14/805* | (2006.01) | |

(52) U.S. Cl.
USPC ............ 530/412; 530/413; 530/416; 530/829

(58) Field of Classification Search
USPC ........................................................ 530/412
See application file for complete search history.

(56) References Cited

U.S. PATENT DOCUMENTS 4,675,384 A * 6/1987 Dromard et al. .............. 530/364

FOREIGN PATENT DOCUMENTS

| FR | 2 234 312 | 1/1975 |
| WO | WO2008/106644 | 9/2008 |
| WO | WO 2008/113589 | * 9/2008 |

OTHER PUBLICATIONS

Cheung, AK, and Parker CJ (1992) Journal of the American Society of Nephrology 2, 1328-1337. "Modualtion of Complement Activation on Hemodialysis Membranes by Immobilized Heparin".*
Lambris, JD and Muller-Eberhard HJ (1984) Journal of Biological Chemistry 256, 12685-12690. "Isolation and Characterization of a 33,000-Dalton Fragment of Complement Factor B with Catalytic and C3b Binding Activity".*
GE HEalthcare Data File 18-1172-88 AB Q Sepharose High Performance SP Sepharose High Performance 2006.*
Lambris et al. "Release of endogenous C3b inactivator from lymphocytes in response to triggering membrane receptors for b1H globulin" 1980 J. Exp. Med. 152 1625-1644.*
McKay et al. "The interaction of heparin with plasma proteins" 1980 J. Lab. Clin. Med. 95, 69-80.*
Nakamura et al., "Purification and Properties of Intracellular Clotting Factor, Factor B, from Horseshoe Crab (*Tachypleus tridentatus*) Hemocytes," J. Biochem., 99: 847-857 (1986).
Williams, S.C. and R.B. Sim, "Dye Ligand Affinity Purification of Human Complement Factor B and $\beta_2$ glycoprotein I," Journal of Immunological Methods, 157:25-30 (1993).
Pang, A.S.D. and W.P. Aston, "The Alternative Complement Pathway in Bovine Serum: The Isolation of a Serum Protein with Factor B Activity," Immunochemistry, 15:529-534 (1978).
International Search Report, PCT/FR2010/052426, mailed Mar. 9, 2011 (3 pages).

* cited by examiner

*Primary Examiner* — Manjunath Rao
*Assistant Examiner* — Gerard Lacourciere
(74) *Attorney, Agent, or Firm* — Cesari and McKenna, LLP

(57) ABSTRACT

The invention relates to a method for purifying factor B, comprising the steps consisting in:
(i) obtaining a blood plasma fraction containing factor B;
(ii) subjecting the fraction obtained in step (i) to a heparin-like affinity chromatography;
(iii) subjecting the factor B-enriched fraction obtained in step (ii) to a cation exchange chromatography;
(iv) subjecting the factor B-enriched fraction obtained in step (iii) to an anion exchange chromatography,
(v) eluting the factor B.

6 Claims, 1 Drawing Sheet

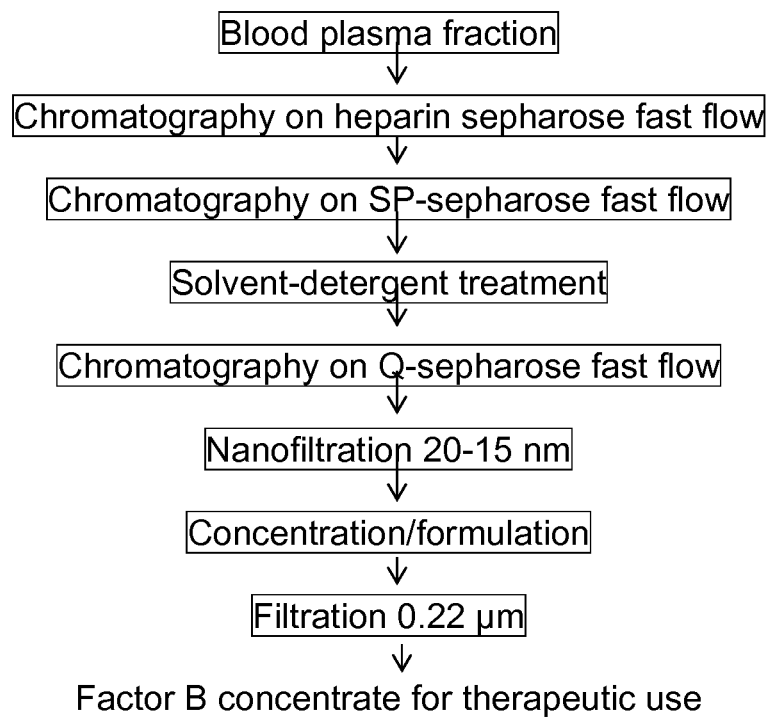

METHOD FOR PURIFYING FACTOR B

CROSS REFERENCE TO RELATED APPLICATIONS

This application is a National Stage of International Application No. PCT/FR2010/052426, filed on Nov. 15, 2010, which claims priority to French Application No. 0958047, filed Nov. 16, 2009. The contents of the prior applications are incorporated herein by reference in their entirety.

The invention relates to a method for purifying factor B from human blood plasma.

TECHNICAL BACKGROUND OF THE INVENTION

Complement plays an essential role in the organism's defence against infectious agents and in the inflammatory process. It represents a helper system for immunity, in particular for the humoral response and for the innate response.

Complement comprises a set of approximately 30 plasma and sometimes membrane proteins, synthesized essentially by the liver and the macrophages and which can be activated by proteolytic cascades. It comprises both plasma proteins, numerous different surface cell receptors, some present on inflammatory cells and others on immune system cells, and also regulatory membrane proteins which protect the host cells against self-attack. The complement plasma proteins operate either as enzymes, or as binding proteins, or as regulators (inhibitors or activators).

There are 3 pathways for triggering the complement cascade: the classical pathway triggered by antibodies, the alternative pathway triggered by bacterial substances in the absence of antibodies, and the pathway dependent on lectins which recognize certain bacterial polysaccharides. The latter two pathways are involved in the innate response and are extremely important in the host's defence against bacterial infections.

Complement factor B is a component of the alternative complement activation pathway. It circulates in the blood as a protein composed of a single polypeptide chain with a molecular weight of 93 kDa. During activation of the alternative pathway, factor B is cleaved by complement factor D, resulting in an inactive Ba chain (30 kDa) and in the Bb catalytic subunit (63 kDa). The Bb active subunit is a serine protease which associates with C3b to form the C3 convertase of the alternative pathway (C3bBb). The Bb subunit is involved in the proliferation of pre-activated B lymphocytes, while the Ba chain inhibits their proliferation.

Factor B preparations would be of use in the treatment of factor B deficiencies, but for the moment, no preparation of this type is commercially available.

SUMMARY OF THE INVENTION

The invention provides a method for purifying factor B, comprising the steps consisting in:
(i) obtaining a blood plasma fraction containing factor B;
(ii) subjecting the fraction obtained in step (i) to a heparin-like affinity chromatography;
(iii) subjecting the factor B-enriched fraction obtained in step (ii) to a cation exchange chromatography;
(iv) subjecting the factor B-enriched fraction obtained in step (iii) to an anion exchange chromatography;
(v) eluting the factor B.

The method may also comprise at least one viral inactivation treatment, preferably via the action of a solvent and detergent, and/or at least one viral removal treatment, preferably by nanofiltration.

A subject of the invention is also a method for obtaining a factor B preparation for therapeutic use, which comprises:
purification of the factor B according to the purification method as defined herein, as a result of which a factor B concentrate is obtained,
followed by steps of formulation, concentration and then filtration of the factor B concentrate.

A subject of the invention is also the factor B preparation that can be obtained by means of this method. Preferably, said preparation is in lyophilized form.

The method of the invention has many advantages: it is industrializable, and makes it possible to purify factor B from various production intermediates, and with a high degree of purity.

FIGURE LEGEND

FIG. 1 shows a scheme representing the purification method steps followed in Example 1.

DETAILED DESCRIPTION OF THE INVENTION

The term "factor B" is intended to mean any protein having the amino acid sequence of native human factor B. The term "factor B" also comprises the natural allelic variations and/or the isoforms of factor B that are found naturally, and any form or degree of glycosylation or other post-translational modification. Also included are the factor B homologues or derivatives which have the same or a greater biological activity compared with the activity of the wild-type form and/or which have a sequence identity of at least 80%, preferably at least 85%, more preferably at least 90%.

The term "biological activity" of factor B includes the ability to activate C3 convertase. The activity of factor B can be measured in various ways, well known to those skilled in the art.

Generally, a chromatography consists in bringing factor B in solution into contact
with a matrix to which factor B binds, optionally washing the matrix under appropriate conditions such that the factor B remains bound, then applying to the matrix a solution which causes elution of the factor B from the matrix,
or, alternatively, with a matrix which binds the impurities but not the factor B.

Step (i) for Obtaining a Blood Plasma Fraction Containing Factor B:

Preferably, the supernatant of a cryoprecipitate of blood plasma optionally mixed with a plasma fraction not retained on an anion exchange chromatography of DEAE-Sephadex type is used as starting material. It is also possible to use the supernatant resulting from an ethanol precipitation. A plasma fraction not retained on an anion exchange chromatography can also be used.

Heparin-like affinity chromatography uses a matrix or a support, which is most commonly agarose gel, onto which heparin or heparin derivatives or mimetics are grafted. Among the heparin-like ligands, mention may in particular be made of the following ligands: chondroitin sulphate, heparan sulphate, dermatan sulphate, keratan sulphate, or synthetic oligomers, for example cellubiose sulphate ester (MATREX™ Cellufine Sulfate), or therapeutic analogues of heparin, for example sulphated oligosaccharides.

Preferably, the pH is adjusted to a value of 6, for example by equilibrating the column with a 20 mM sodium phosphate buffer solution, with an osmolality of 60±5 mOsm/kg, and a pH 6.0±0.1.

An example of a particular protocol is presented in Example 1.

This step makes it possible to bind factor B and antithrombin III (AT III), and to elute them separately.

Cation Exchange Chromatography Step (iii):

Cation exchange chromatography uses a matrix, most commonly of agarose or polymeric type, onto which are grafted ligands such as carboxymethyl (CM), sulpho-propyl (SP) or methyl sulphonate (S). Cation exchange supports are commercially available: mention may, for example, be made of CM-Sepharose, SP-Sepharose and S-Sepharose (GE Healthcare), Toyopearl CM-650 and Toyopearl SP-650 (Tosoh Biosciences), Fractogel EMD SO3 and Fractogel EMD COO (Merck KGaA), Macro-Prep CM Support and Macro-Prep High S Support (BioRad), and CM HyperD, S HyperD, CM Trisacryl, SP Trisacryl and SP Sperodex (all Pall) supports.

Preferably, SP Sepharose FF is used. An example of a particular protocol is presented in Example 1.

Anion Exchange Chromatography Step (iv):

Factor B can, under certain conditions, bind to anion exchange resins, and be desorbed therefrom using buffer systems with a high ionic strength.

Anion exchange chromatography uses a matrix, most commonly of agarose or polymeric type, onto which are grafted ligands such as diethylaminoethyl (DEAE), quaternary aminoethyl (QAE) or quaternary ammonium (Q). Anion exchange supports are commercially available: mention may, for example, be made of DEAE-Sepharose and Q-Sepharose (GE Healthcare), Toyopearl DEAE-650 and Toyopearl Super Q-650 (Tosoh Biosciences), Fractogel EMD DEAE and Fractogel EMD TMAE (Merck KGaA), Macro-Prep DEAE Support and Macro-Prep High Q Support (BioRad), and DEAE HyperD, Q HyperD, DEAE Trisacryl and DEAE Sperodex (all Pall) supports. Q Sepharose FF is preferably used.

An example of a particular protocol is presented in Example 1.

The factor B is eluted by increasing the ionic strength of the anion exchange chromatography equilibration buffer.

Advantageously, the pH of the blood plasma fraction containing factor B and obtained in step (i) is adjusted so as to be included in the range of from pH 5.5 to pH 6.5 and preferably so as to be equal to pH 6.0. Advantageously, the pH of the eluted fraction from step (ii) which is then diluted before step (iii) is adjusted so as to be included in the range of from pH 5.5 to pH 7.5. More advantageously, the pH of the eluted fraction from step (iii) which is then diluted before step (iv) is adjusted so as to be included in the range of from 5.5 to 7.5.

According to one preferred embodiment of the invention, the factor B purification comprises the steps consisting in:
(i) obtaining a plasma fraction containing factor B, for example (a) the supernatant of a blood plasma cryoprecipitate optionally mixed with a plasma fraction not retained on an anion exchange chromatography; or else, for example, (b) a fraction not retained on an anion exchange chromatography;
(ii) subjecting said supernatant, or said fraction not retained on an anion exchange chromatography, to a heparin-like affinity chromatography, for example on sepharose gel onto which heparin is grafted, as a result of which a factor B-enriched fraction is obtained;
(iii) (a) subjecting the fraction obtained in step (ii) to a cation exchange chromatography, for example on SP-Sepharose;
(iii) (b) followed, where appropriate, by a treatment with solvent and detergent;
(iv) subjecting the factor B-enriched fraction obtained in step (iii) (a) or (b) to an anion exchange chromatography, for example on Q-Sepharose.

In order to obtain a preparation for therapeutic use, the method is generally continued by means of steps of formulation, concentration, and then filtration of the factor B concentrate.

More specifically, the method for producing a factor B preparation according to the invention can comprise the following steps:
(i) obtaining a plasma fraction containing factor B, for example the supernatant of a blood plasma cryo-precipitate optionally mixed with a plasma fraction not retained on an anion exchange chromatography, or, for example, a plasma fraction not retained on an anion exchange chromatography;
(ii) subjecting said supernatant, or said fraction not retained, to a heparin-like affinity chromatography, for example on sepharose gel onto which heparin is grafted; washing then eluting the factor B with a buffer having an ionic strength greater than that of the heparin-like affinity chromatography equilibration buffer, diluting the eluted fraction, then
(iii) (a) subjecting it to a cation exchange chromatography, for example on SP-Sepharose; washing then eluting the factor B with a buffer having an ionic strength greater than that of the cation exchange chromatography equilibration buffer, diluting the eluted fraction, then
(iii) (b) where appropriate, subjecting it to a treatment with solvent and detergent;
(iv) then subjecting it to an anion exchange chromatography, for example on Q-Sepharose;
(v) washing and eluting the factor B, generally with a buffer having an ionic strength greater than that of the anion exchange chromatography equilibration buffer;
(vi) preparing a factor B concentrate.

Other possible steps:

Preferably, the chromatography of step (ii) is the only heparin-like affinity chromatography, the method not comprising any additional heparin-like affinity chromatography step.

In one preferred embodiment, the method of the invention contains no chromatography other than those provided for in steps (ii) to (iv) defined above. However, the method of the invention can optionally comprise additional steps, for example other anion or cation exchange chromatographies, but also, where appropriate, one or more hydrophobic interaction chromatographies.

Factor B can, under certain conditions, bind to hydrophobic interaction chromatography resins, and be desorbed therefrom using buffer systems with a low ionic strength.

Such chromatography uses a matrix, most commonly of agarose or polymeric type, onto which are grafted ligands such as phenyl, octyl, butyl, methyl or else hexylamine, phenylpropylamine or 4-mercaptoethyl-pyridine. Supports for this type of chromatography are commercially available: mention may, for example, be made of phenyl sepharose, octyl sepharose, butyl sepharose, CAPTO™ MMC multimodal cation exchanger (all GE Healthcare), Toyopearl Phenyl-650, Toyopearl Butyl-650 and Toyopearl Hexyl-650 (all Tosoh Biosciences), Macro-Prep Methyl HIC Support and Macro-Prep t-Butyl HIC Support (Bio-Rad) and HEA Hyper-Cel, PPA HyperCel and MEP HyperCel (all Pall) supports.

The method of the invention can also comprise a hydroxyapatite-like chromatography. Indeed, the factor B can be purified using composites of calcium phosphate, fluoroapatite or hydroxyapatite as solid phase. Among the commercially available supports, mention may, for example, be made of Bio-Gel Hydroxyapatite HT (Bio-Rad), ceramic fluoroapatite and ceramic hydroxyapatite (Bio-Rad), and HA Ultrogel (Pall).

The method of the invention may further comprise an immunoaffinity chromatography, which uses, for example, the antibodies or aptamers immobilized on a chromatography matrix. The matrices are generally resins that have been preactivated, for example with epoxy (Sepharose 6B1, EAH Sepharose 4B, Amino Sepharose 6 FF, 6-AKS Sepharose 4FF, Toyopearl AF Epoxy, Toyopearl AF amino, Toyopearl AF Tresyl). The unbound impurities are washed away using suitable buffer systems (citrate buffer, phosphate buffer or HEPES, for example), and the factor B is then eluted using, for example, high concentrations of chaotropic salts (of lithium bromide, thiocyanate type), of low-pH (glycine, pH 2-3) or high-pH (TRIS, pH 9) buffer systems.

The method of the invention may also include other treatments, such as a delipidation. Delipidation consists in removing, preferably upstream or as early as possible in the method, lipid impurities from protein solutions by means, for example, of precipitation or of adsorption. Suitable precipitating agents include, for example, polyethylene glycols (PEGs) or ammonium sulphate, while silica powders ("fumed silica", Aerosil 200, Aerosil 380), dextran sulphates or fluorocarbons (Freon-113) are suitable adsorbents.

It may also be advantageous to remove or inhibit the proteolytic impurities, namely the enzymes, for example the proteases or glycosidases, that would be capable of cleaving the factor B molecule into inactive truncated forms. This removal or inhibition is preferably carried out as early as possible, more preferably upstream of the purification method. For this, a chromatographic method can be used in which protease inhibitors are immobilized on matrices of agarose or polymeric matrix type. A filter which retains some of the proteolytic impurities (such as the cellulose SARTOCLEAR® filter) may also be used.

Such protease inhibitors may, for example, be benzamidine, 4-aminobenzamidine, benzamidine hydrochloride and its derivatives, lysine and its derivatives, 6-aminohexanoic acid (ε-aminocaproic acid) and its derivatives, trans-4-aminomethylcyclohexanecarboxylic acid (tranexamic acid) and its derivatives, 4-(2-aminoethyl)benzenesulphonyl fluoride (AEBSF) and its derivatives, (4-aminophenyl)methanesulphonyl fluoride (APMSF) and its derivatives, 3,4-dichloroisocoumarin (DCI) and its derivatives, acetyl-leucyl-leucyl-arginal (leupeptin) and its derivatives, aprotinin and its derivatives, soybean trypsin inhibitor and its derivatives, α2-antiplasmin and its derivatives, thrombin inhibitors (in particular antithrombin III) and its derivatives. Commercially available chromatography supports are, for example, ECH Lysine Sepharose 4B, Benzamidine Sepharose 6B (GE Healthcare), and p-Aminobenzamidine Agarose 6XL (Prometic).

Rather than being removed, the proteolytic impurities can be inhibited by adding one or more protease inhibitors of the group mentioned above, in particular antithrombin III and C1-inhibitor, and then by removing the enzyme/inhibitor complex by means of subsequent purification steps.

Another approach for removing the proteolytic impurities is to use immobilized dyes, such as Cibacron Blue F3GA or its derivatives, other triazine dyes, such as Procion Red HE-3B and its derivatives, or Procion Green H-4G and its derivatives, Reactive Red 120 and its derivatives, Reactive Green 19 and its derivatives, Reactive Yellow 86 and its derivatives, or Reactive Orange 14 and its derivatives, immobilized on matrices of agarose or polymeric matrix type.

Virus Inactivation

The factor B preparation that is of use in the invention has generally undergone at least one step of removing or inactivating at least one infectious agent. Among the infectious agents, mention may be made of viruses and NCTAs (non-conventional transmissible agents) such as the prion. Viral inactivation often comprises treatment with chemical products, for example with solvent, detergent, and/or with heat, for example by pasteurization. Nanofiltration is also of use for removing an infectious agent. Preferably, the method comprises at least one treatment with solvent and detergent, and a nanofiltration.

Pasteurization refers to methods which expose the liquid factor B compositions to a temperature of 60° C. for at least 10 h.

The treatment with solvent and/or detergent (generally referred to as solvent/detergent treatment) comprises in particular treatment with tri-n-butyl phosphate TnBP and/or a detergent which is chosen from Triton X-100, Tween (preferably Tween 80) and sodium cholate. The treatment is generally carried out at 25° C. for at least 6 h.

Nanofiltration generally refers to the filtration of a factor B solution through a filter with a pore size of less than 80 nm. Available filters are, for example, cuprammonium regenerated cellulose filters PLANOVA™ 75 nm, PLANOVA™ 35 nm, PLANOVA™ 20 nm or PLANOVA™ 15 nm, BioEX (Asahi Corporation), Ultipor DV 50 or DV 20 (Pall Corporation), Virosart CPV (Sartorius), Viresolve NFR or NFP (Millipore). Preferably, a nanofiltration is carried out after the anion exchange chromatography step (iv). In one particular embodiment, the purified factor B fraction is filtered on a sequence of filters with a pore size of 20 nm and 15 nm.

Formulation

In order to obtain factor B preparations for therapeutic use which are stable, the factor B preparation obtained is formulated with suitable excipients and stabilizers. These may be diluents, cyroprotective agents, lyoprotective agents, etc.

Among the conventional lyoprotectants, mention may be made of sugars (sucrose, trehalose, glucose, lactose, etc.), polyols (mannitol, sorbitol) and amino acids (glycine, arginine, histidine, alanine) which can be used at a concentration of between 0 and 10%. Surfactants of polysorbate (Tween 20 or Tween 80 for example), poloxamer (for example poloxamer 188) or polyethylene glycol type can also be added.

Antioxidants (for example methionine, monothioglycerol, glutathione, citric acid, ascorbic acid, sodium metabisulphite and sodium sulphite) may also be added.

Buffer substances may also be used, for example in the form of carbonate, phosphate, citrate, acetate, borate, trimethamine [(2-amino-2-(hydroxymethyl)propane-1,3-diol), TRIS], glycine and lysine.

Desiccation

The liquid factor B formulation can undergo desiccation if necessary, in order to obtain a solid form.

Desiccation is a process for extensive removal of water. It is a dehydration aimed at removing as much water as possible. This phenomenon may be natural or forced. This desiccation can be carried out by means of lyophilization, spray-drying or cryo-spray-drying techniques. The preferred method for obtaining the solid form of the composition for pharmaceutical use according to the invention is lyophilization.

Lyophilization methods are well known to those skilled in the art, see, for example Wang et al., Lyophilization and development of solid protein pharmaceuticals, International Journal of Pharmaceutics, Vol. 203, p. 1-60, 2000.

Other methods suitable for reducing the degree of moisture or the water content of the composition can be envisaged. Preferably, the degree of moisture is less than or equal to 3% by weight, preferably less than or equal to 2.5%, more preferably less than or equal to 2%, preferably less than or equal to 1.5%.

The solid composition can be dissolved in water for injection (WFI) or in a reconstituting solvent, so as to obtain a formulation for therapeutic use.

The figure and the examples illustrate the invention without limiting the scope thereof.

EXAMPLES

Example 1

Factor B Purification

A factor B concentrate is prepared according to the steps represented in the attached figure.

Cryosupernatant is prepared by thawing fresh plasma frozen at a temperature between 1° C. and 6° C. (cryoprecipitation). After centrifugation, the cryoprecipitate is recovered in order to produce the fibrinogen, von Willebrand factor and factor VIII concentrates. The supernatant is collected, of which a part is subjected to a purification step on DEAE-Sephadex in order to bind the vitamin K-dependent factors, such as protein C, factor VII and factor IX. The fraction not retained on DEAE-Sephadex is mixed with the remaining cryosupernatant so as to constitute solution A. The factor B concentration in the fraction is approximately 100-150 µg/ml (for a recorded plasma concentration of 200 µg/ml).

Solution A is adjusted to a pH of between 5.5 and 6.5, and preferably to 6.0. The adjusted fraction is then subjected to a chromatography on a Heparin Sepharose FF column or other chromatographic support onto which a heparin ligand is grafted. Most of the plasma proteins are found, not retarded, in the chromatography filtrate. After washing of the gel until a return to the baseline is obtained, the factor B is eluted by increasing the ionic strength of the column equilibration buffer. The eluted fraction is diluted, and then chromatographed on a strong cation exchange column of SP Sepharose FF type or equivalent. After washing the gel, the proteins weakly adsorbed onto the gel are eluted by increasing the ionic strength of the column equilibration buffer. The factor B is eluted by even further increasing the ionic strength of the column equilibration buffer. The eluted fraction is then subjected to a viral inactivation step by solvent/detergent treatment (Polysorbate 80 and TnBP) which is effective on enveloped viruses. The fraction is then diluted, adjusted to a pH of 6.0 (assay 1) or 6.5 (assay 2), and then subjected to a chromatography on a strong anion exchange column of Q Sepharose FF type or equivalent, equilibrated at pH 6.0 or 6.5. After washing of the gel until a return to the baseline is obtained, the factor B is eluted by increasing the ionic strength of the column equilibration buffer. The factor B fraction obtained at this stage is of very high purity and can be subjected to a step of viral removal by nanofiltration, and then concentrated and formulated by ultrafiltration.

Example 2

Purity Tests

Samples of the factor B fractions undergoing purification were taken at the end of each of the steps indicated in Example 1.

Purification Tests

The factor B is assayed conventionally by means of an immunoenzymatic method (ELISA) with commercial reagents (Diagnostica Stago). Briefly, the factor B to be assayed is captured by an anti-human factor B antibody immobilized on a solid phase. The factor B bound is then recognized by a peroxidase immunoconjugate. The amount of peroxidase bound is measured by its activity on the substrate ortho-phenylenediamine in the presence of aqueous hydrogen peroxide. The strength of the coloration, after the reaction has been stopped with a strong acid, depends on the amount of factor B initially present in the sample. The factor B thus assayed is called "factor B antigen" or "Ag".

The purification results are indicated in the table below.

TABLE 1

Purification of factor B from solution A

| Step | Yield (%) | | Purity (Ag/Prot) | |
|---|---|---|---|---|
| Starting solution A | 100 | | 0.002 | |
| $1^{st}$ purification step on heparin-Sepharose FF | 22 | | 0.038 | |
| $2^{nd}$ purification step on SP-Sepharose FF | 81 | | 0.068 | |
| $3^{rd}$ purification step on Q-Sepharose FF | Assay 1 60 | Assay 2 100 | Assay 1 0.85 | Assay 2 0.84 |

The invention claimed is:

1. A method for purifying factor B, the method comprising:
   (i) obtaining a blood plasma fraction containing factor B;
   (ii) subjecting the fraction obtained in step (i) to affinity chromatography on a sepharose gel onto which heparin is grafted and collecting a factor B-enriched fraction;
   (iii) subjecting the factor B-enriched fraction obtained in step (ii) to cation exchange chromatography on SP-Sepharose, collecting a fraction further enriched in factor B, and treating the fraction further enriched in factor B with solvent and detergent;
   (iv) subjecting the treated fraction further enriched in factor B obtained in step (iii) to anion exchange chromatography on Q-Sepharose; and
   (v) eluting the factor B,
wherein the blood plasma fraction containing factor B is obtained from the supernatant of a blood plasma cryoprecipitate optionally mixed with a plasma fraction not retained on an anion exchange chromatography, or a plasma fraction not retained on an anion exchange chromatography, and the blood plasma fraction containing factor B is adjusted to a pH of 6 prior to step (ii).

2. A method for purifying factor B, the method comprising:
   (i) obtaining a blood plasma fraction containing factor B;
   (ii) subjecting the fraction obtained in step (i) to affinity chromatography on a sepharose gel onto which heparin is grafted and collecting a factor B-enriched fraction;
   (iii) subjecting the factor B-enriched fraction obtained in step (ii) to cation exchange chromatography on SP-Sepharose, collecting a fraction further enriched in factor B, and treating the fraction further enriched in factor B with solvent and detergent;

(iv) subjecting the treated fraction further enriched in factor B obtained in step (iii) to anion exchange chromatography on Q-Sepharose; and (v) eluting the factor B, wherein the blood plasma fraction containing factor B is obtained from the supernatant of a blood plasma cryoprecipitate optionally mixed with a plasma fraction not retained on an anion exchange chromatography, or a plasma fraction not retained on an anion exchange chromatography, the blood plasma fraction containing factor B is adjusted to a pH of 6 prior to step (ii), and the affinity chromatography step (ii) is the only heparin-like affinity chromatography step in the method.

3. The method of claim 1, further comprising a viral removal treatment.

4. The method of claim 3, wherein the viral removal treatment is nanofiltration.

5. The method of claim 2, further comprising a viral removal treatment.

6. The method of claim 5, wherein the viral removal treatment is nanofiltration.

* * * * *